United States Patent [19]

Kopito et al.

[11] 3,979,945

[45] Sept. 14, 1976

[54] ECCENTRIC VISCOMETER FOR TESTING BIOLOGICAL AND OTHER FLUIDS

[75] Inventors: Louis Kopito, Brookline; Samuel R. Schuster, Wellesley; Harold Kosasky, Brookline, all of Mass.

[73] Assignee: Ovutime, Inc., Brookline, Mass.

[22] Filed: Apr. 30, 1975

[21] Appl. No.: 573,348

[52] U.S. Cl. ............................ 73/60; 23/230 B; 73/9; 73/54; 128/2 W
[51] Int. Cl.² .................. G01N 11/00; G01N 33/16
[58] Field of Search ............... 73/54, 59, 60, 9, 10, 73/53; 128/2 W; 23/230 B

[56] References Cited
UNITED STATES PATENTS

| | | | |
|---|---|---|---|
| 1,184,880 | 5/1916 | Schleher, Jr. | 73/10 |
| 2,427,289 | 9/1947 | Lancaster | 73/9 X |
| 2,878,670 | 3/1959 | Martin | 73/60 |
| 2,953,016 | 9/1960 | Seitz, Jr. | 73/60 |
| 3,115,034 | 12/1963 | De Hart | 73/60 X |
| 3,552,198 | 1/1971 | Friedland | 73/9 X |

OTHER PUBLICATIONS

Benis; A. M. et al., *Rheology of Biological Systems*, III, Thomas, 1973, Chap. 9, pp. 218–259.

*Primary Examiner*—Richard C. Queisser
*Assistant Examiner*—Joseph W. Roskos
*Attorney, Agent, or Firm*—Morse, Altman, Oates & Bello

[57] ABSTRACT

A device for determining the rheological properties of a liquid comprises an inner bearing member having a horizontally disposed outer cylindrical surface and an outer bearing member having a horizontally disposed inner cylindrical surface, each cylindrical surface constituting a bearing surface of predetermined grit. A liquid sample is introduced between the inner and outer cylindrical surfaces, which are disposed eccentrically relative to one another. Relative mechanical movement of the members, which is related to both shear and displacement of the liquid disposed between them, provides an indication of the rheological properties of the liquid.

14 Claims, 8 Drawing Figures

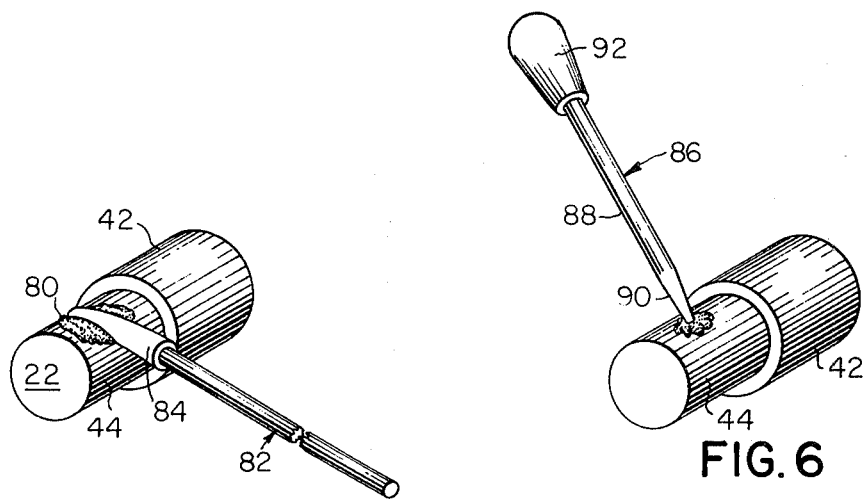
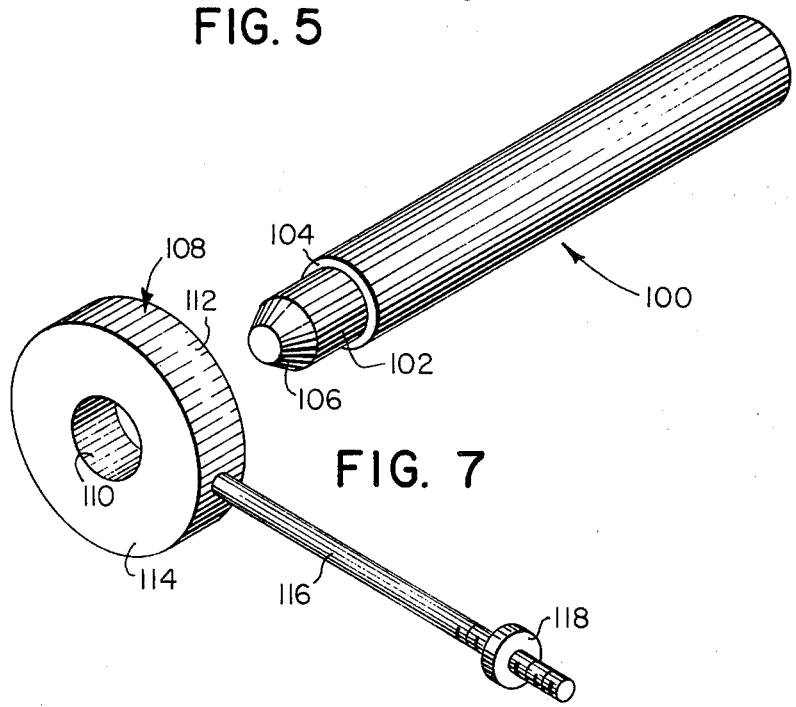
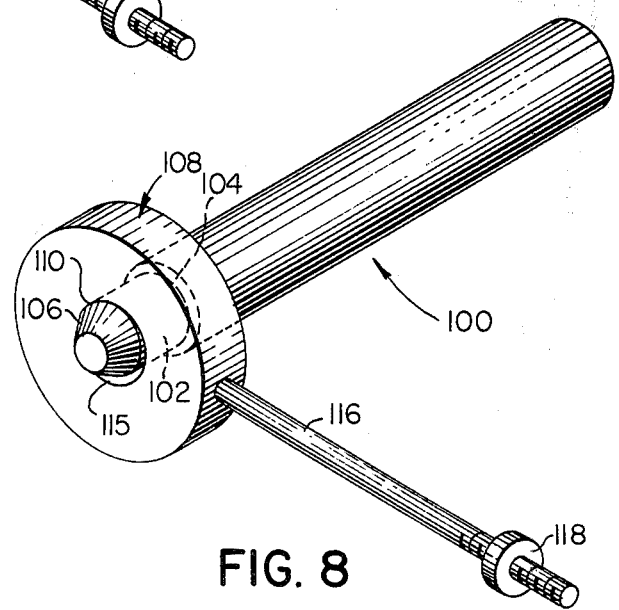

ECCENTRIC VISCOMETER FOR TESTING BIOLOGICAL AND OTHER FLUIDS

CROSS-REFERENCE TO RELATED APPLICATIONS

The assignee of this application is the assignee of pending application Ser. No. 523,047, filed Nov. 12, 1974 for Mucus Testing Processes And Devices.

BACKGROUND OF THE INVENTION

1. Field of Invention

The present invention relates to processes and devices for determining rheological properties of biological and other liquids. More specifically, the present invention is directed towards processes and devices for obtaining bodily mucus, chiefly cervical mucus and/or oral mucus, and for determining its viscoelastic properties in order to predict and indicate the inception and the presence of ovulation for conception control.

2. Description of the Prior Art

It has been found that mucus samples from the vaginal and oral cavities undergo distinct in-phase rheological changes during the menstrual cycle. Although the changes in the cervical mucus are much more noticeable than the changes in the oral mucus, both changes are readily determinable. During the immediate preovulatory phase under estrogen domination for a period of one to three days, the mucus is profuse and watery. During the postovulatory phase, under progestation, the mucus becomes less abundant and highly viscous. In healthy women with normal menstrual cycles, as is well documented in the medical literature, ovulation usually occurs between the 12th and 14th day prior to the next menstrual period. Specifically, cervical mucus is most hydrated (97 to 98 percent water) at the time of ovulation and is relatively dehydrated (80 to 90 percent water) at other times. The solid residue present after desiccation may range from 2 percent during ovulation to 20 percent at other times, a ten fold increase. Determining ovulation on the basis of the preceeding menstrual period, such as in the rythm method of counting the days ellapsed between the termination of the menstrual period and the presumed midcycle ovulatory phase, is prone to errors because of the great variability in the length of the proliferative period, i.e. between the end of the menses and ovulation. Although it is possible to predict ovulation on the basis of hormonal changes in the blood or chemical changes in the mucus, present procedures for such analyses besides being lengthly and costly, do not provide immediate result. In consequence, these procedures are utilized only in special cases. At present, there are no known reliable on-the-spot techniques that are capable of providing the information necessary for prediction or confirmation of ovulation during or immediately following examination of a patient.

SUMMARY OF THE INVENTION the primary object of the present invention is to provide processes and devices for determining the rheological properties of biological and other liquids. Generally, the device comprises an inner bearing member having a horizontally disposed outer cylindrical surface and an outer bearing member having a horizontally disposed inner cylindrical surface, each cylindrical surface constituting a bearing surface of predetermined grit. A liquid sample is introduced between the horizontally disposed outer cylindrical surface of the inner bearing member and the horizontally disposed inner cylindrical surface of the outer bearing member, the cylindrical surfaces being eccentrically oriented relative to one another. One bearing member is fixed and the other bearing member is biased. Relative mechanical movement of the bearing members, a rotational movement about eccentric bearing surface axes that is related to both shear and displacement of the liquid sample, provides an indication of the rheological properties of the liquid.

It is another object of the invention to provide processes and devices for obtaining and testing a bodily mucus sample in order to determine menstrual cycle phase by introducing the mucus sample between a horizontally disposed outer cylindrical surface of an inner bearing member and a horizontally disposed inner cylindrical surface of an outer bearing member, the cylindrical surfaces being eccentrically oriented relative to one another. One bearing member is fixed and the other bearing member is biased, each cylindrical surface constituting a bearing surface of predetermined grit. Mechanical movement or the absence of such movement of the biased bearing member relative to the fixed bearing denotes the menstrual cycle phase and provides indicia of ovulation. The inner and outer bearing members are individually separable from each other and from a support so that they can be sterilized or replaced. The motion between the bearing members is a rotational movement about eccentric bearing surface axes, each of which is horizontally disposed. Ordinarily, the mucus is supplied to one of the bearing surfaces while the bearing members are disassembled from each other and the mucus is extruded between the bearing surfaces when they are assembled with each other. In one form, one of the bearing members is fixed on a suitable support and the other is provided with a biasing member, e.g. a weight or a spring, which exerts sufficient force to cause relative movement when the highly fluid mucus has been sampled during the ovulatory phase but insufficient force to cause relative movement when the viscous mucus has been sampled at other times during the menstrual period. In another form, one of the bearing members is an extension of an elongated probe, which is inserted into the vaginal cavity and held against the external os. for retrieval of a cervical mucus specimen. In accordance with the present invention, it has been discovered that the foregoing operation requires that the bearing members have inner and outer bearing surfaces, each characterized by a surface finish having valleys and peaks of from 8 to 125 microinches in average valley to peak height. Such a surface finish, in various embodiments, is provided by precision grinding, machining or etching random valleys and peaks or machining or etching regularly spaced prismatic facets or the like. It is believed that this specific surface roughness controls slippage of the mucus with respect to the bearing surfaces and ensures the occurrences of predetermined shear within the mucus interior and displacement of the mucus between the eccentric surfaces.

Other objects of the present invention will in part be obvious and will in part appear hereinafter.

The invention accordingly comprises the processes and devices, together with their steps, parts and interrelationships, which are exemplified in the present disclosure, the scope of which will be indicated in the appended claims.

BRIEF DESCRIPTION OF THE DRAWINGS

For a fuller understanding of the nature and objects of the present invention, reference is made to the following detailed description, which is to be taken in connection with the accompanying drawings, wherein:

FIG. 5 illustrates an auxilliary instrument useful in the performance of certain steps of the present invention;

FIG. 6 illustrates another auxilliary instrument useful in the performance of certain steps of the present invention;

FIG. 7 is a perspective view of another device embodying the present invention, with parts disassembled for the performance of certain steps of the process of the present invention; and FIG. 8 is a perspective view of the device of FIG. 7, with parts assembled for the performance of other steps of the present invention.

DETAILED DESCRIPTION OF THE PREFERRED EMBODIMENTS

The present invention provides processes and devices for determining the rheological properties of biological and other liquid involving horizontally disposed bearing surfaces that are eccentrically oriented with respect to one another. The basic principles of operation are believed to involve; (1) the shear of a liquid between two coaxial rotating surfaces and (2) the displacement of liquid through the eccentric disposition of two bearing surfaces which relates to resistance flow measurements in capillary viscometry. The shear and displacement of the liquid occur at the same time.

Figure 1:
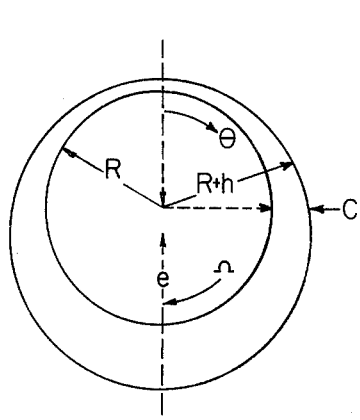
FIG. 1 illustrates certain principles of the invention.

Parameters illustrating certain principles of the invention as shown in FIG. 1, wherein $R$ = radius of inner cylinder
$R + h$ = radius of outer cylinder
$c$ = clearance
$\Omega$ = angular velocity or displacement
$\theta$ = angle between a radius vector and the Z axis
$e$ = eccentricity
$h$ = film thickness The film thickness $h$ depends both upon the clearance $c$ and upon the eccentricity $e$. For $c/R << 1$ $$h = c(1 + \epsilon \cos \theta)$$

where
$\epsilon$ is the eccentricity ratio $e/c$

In the present case, the radii, angular displacement (maximum of 90°) and clearances are known as priori, but the viscosity and eccentricity ratio are not. Experimental data indicates that the eccentricity ratio is determined from the weight per unit area of the outer cylinder and the viscosity of the liquid measured, there being no relative motion between the cylinders and the liquid in immediate contact with the cylinders. The eccentricity ratio is a constant when designing the instrument and becomes variable when a liquid is introduced between the cylinders. In operation, the eccentricity decreases for liquids characterized by low viscosity and increases for liquids characterized by high viscosity. Experimental data shows that the eccentricity ratio is larger for saliva than for cervical mucus using the same weight cylinder. By selecting outer cylinders of predetermined mass, measurements within certain viscosity ranges may be performed under near-optimal conditions for eccentricity ratio $\epsilon$ torque to yield the largest numerical valves.

In a coaxial viscometer, the coefficient of viscosity is defined as $$\eta = M/\Omega$$

where
$\eta$ = viscosity
$M$ = torque (moment)
$\Omega$ = angular displacement in radians or angular velocity In a capillary-tube viscometer, the volume displaced per second is defined as $$V = \Delta P/\eta$$

where
$V$ = displaced volume per second
$\Delta P$ = pressure difference

In the present case $\Delta P$ is operationally analagous to $M$ and $$\eta = \Delta P/V$$

In eccentric viscometry, the equation defining the coefficient of viscosity for a coaxial viscometer and the equation defining volume displaced per second for a capillary-tube viscometer combine to yield $$\eta = M'/\Omega$$

where
$M' = (f) V$ as well as coaxial moment.

Figure 2:
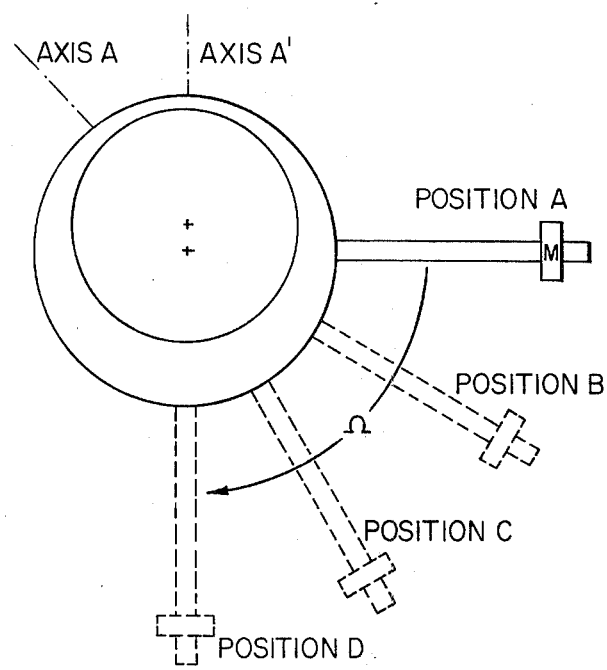
FIG. 2 illustrates certain principles of the invention.

As illustrated in FIG. 2, if the moment M is constant, the viscosity $\eta$ of a liquid between the eccentric cylinder is obtained as a function of angular displacement. No angular displacement, position A as shown by the solid lines in FIG. 2, denotes that the moment is insufficient to overcome the viscosity of the liquid and provides an indication that the viscosity is high. Maximum angular displacement, position D as shown by the dashed lines, denotes that the moment is sufficient to overcome the viscosity of the liquid and provides an indication that the viscosity is low. Intermediate positions B and C reflect values between the two and serve to indicate the approaching time of minimal viscosity.

Figure 3:
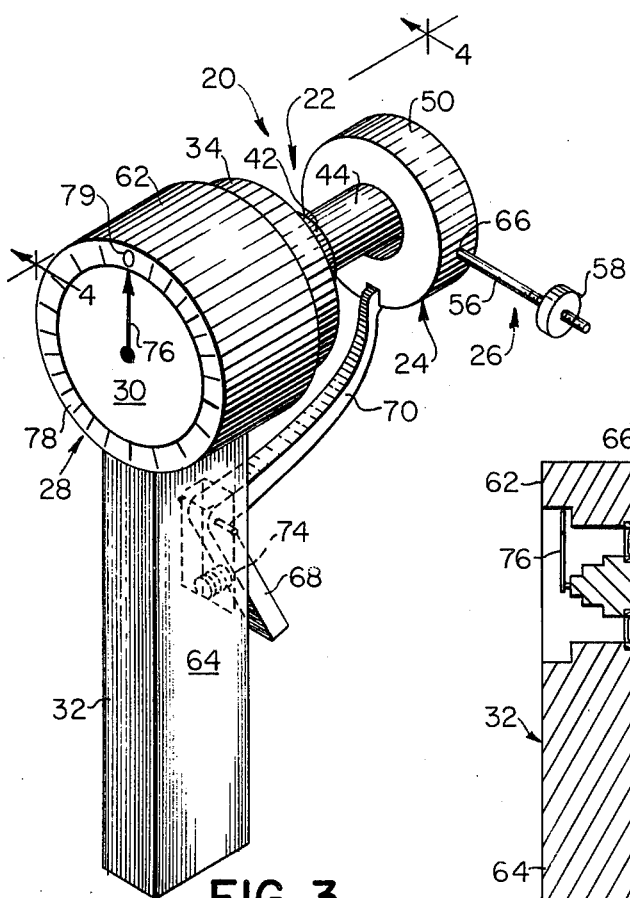
FIG. 3 is a perspective view of a device embodying the present invention, with parts assembled for the performance of certain steps of a process of the present invention.
Figure 4:
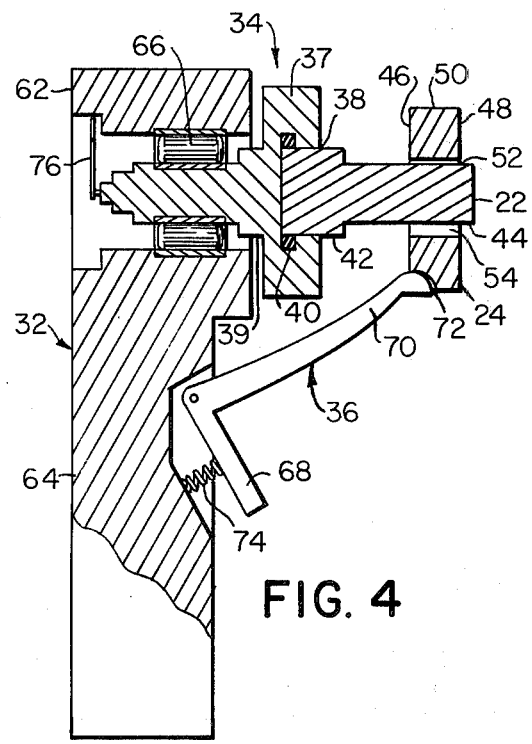
FIG. 4 is a sectional of the device of FIG. 3.

Referring now to FIGS. 3 and 4, there is shown an eccentric viscometer 20 in the form of a torque-gauge comprising an inner bearing member 22, an outer bearing member 24, a biasing member 26, a support 28, and indicia 30. Support 28, which includes a grip 32, a chuck 34 and a release mechanism 36, is composed of a suitable plastic such as methyl methacrylate or polycarbonate. Chuck 34 includes a cylindrical head 37 and a rearwardly extending shaft 39. Head 37 is provided with a horizontally extending central opening 38 having a holder 40, example an "O" ring.

Inner bearing member 22 is in the form of a short cylindrical rod having along its axis a rearward extension 42 and a forward cylindrical outer bearing surface 44. Extension 42, which removably fits into opening 38 and is snugly held therein by holder 40, maintains a horizontal orientation of the axis of bearing member 22 when bearing member 22 and support 28 are assembled. Outer bearing member 24 is in the form of a ring having an axis along which are disposed forward and rearward parallel flat faces 46, 48 an outer cylindrical periphery 50 and an inner cylindrical bearing surface 52. Outer bearing surface 44 and inner bearing surface 52 snugly and rotatably fit each other when bearing members 22 and 24 are assembled. The bearing surfaces are oriented substantially horizontal and are disposed eccentrically relative to one another, whereby a crescent shape gap 54 is formed between outer bearing surface 44 and inner bearing surface 52 when bearing members 22 and 24 are assembled, the gap being shown somewhat exaggerated for clarity. That is, the weight of outer bearing member 24 is such that the upper regions of horizontally disposed outer bearing surface 44 of inner bearing member 22 is urged towards the upper regions of horizontally disposed inner bearing surface 52 of outer bearing member 24, gap 54 being formed between the lower regions of the bearing surfaces. The eccentrically disposed bearing members 22 and 24 define a horizontally disposed eccentric viscometer, the operation of which is dependent upon the weight of outer bearing member 24 and the non-uniform and the changeable dimensions of gap 54.

In accordance with the present invention, each of bearing surfaces 44, 52 requires a surface finish ranging from 8 to 125 microinches in average valley to peak height. Also, the difference between the diametral profiles of the bearing surfaces ranges from 0.01 to 10.0 mils and preferably from 1 to 5 mils. Preferably the axial thickness of outer bearing member 22 ranges from ¼ to 2 inches. The weight of outer bearing member 22 is in the range of 5 to 500 grams and preferably from 10 to 50 grams. In one example, using oral mucus, the weight of outer bearing member 22 is 10 grams. In another example, using cervical mucus, the weight of outer bearing member 22 is 48 grams. preferably each of the bearing members is composed of a dimensionally stable, sterilizable material, for example, a vitreous material such as glass, a metallic material such as stainless steel, or a plastic material such as methyl methacrylate.

Biasing member 26 includes an externally threaded rod 56 and an internally threaded weighted ring 58. Rod 56, which is composed of plastic or metal for example, is frictionally secured within a bore 60 that extends through periphery 50 of outer bearing member 24. Ring 58, which is composed of plastic or metal for example, is turned onto rod 56. The position of ring 58 with respect to the axis of outer bearing member 24 can be adjusted precisely by turning the ring onto rod 56.

Grip 32 inclues a head 62 and a handle 64. Shaft 39 of chuck 34 is freely rotatable within a bearing 66 that is mounted to head 62. Release mechanism 36, which includes a trigger 68 and an extending arm 70, is pivotally mounted to handle 64. The tip of arm 70, which defines a brake, is received within a notch 72 that is formed in outer bearing member 24. When arm 70 and notch 72 are engaged, release mechanism 36 is in the locked position and when arm 70 and notch 72 are disengaged, release mechanism 36 is in the unlocked position. Release mechanism 36 is is biased in the locked position by means of a spring 74 which is mounted to trigger 68, the locked position being shown in FIG. 3. When trigger 68 is pulled inwardly against spring 74, arm 70 disengages notch 72 and outer bearing member 24 is rotatable with respect to inner bearing member 22, release mechanism being in the unlocked position.

Indicia 30 include an outwardly directed arrow 76 on the free end of shaft 39 and a scale 78 on a rearward face of head 62, scale 78 being marked in gram - cm. When the inner and outer bearing members are assembled with mucus between their bearing surfaces and the release mechanism is in the locked position, weighted ring 58 is in a position to cause rotary motion of the outer bearing member with respect to the inner bearing member when the release mechanism is actuated to the unlocked position. Initially, arrow 76 is pointing upwardly towards the zero marking on scale 78 as shown at 79. The arrangement is such that when the mucus between the bearing surfaces is highly watery, weighted ring 58 rotates outer bearing member 24 in a clockwise direction and arrow 76 remains pointed upwardly. On the other hand, when the mucus is highly viscous, weighted ring 58 is incapable of rotating outer bearing member 24, whereby arrow 76 moves clockwise 90° due to the rotational resistance. The angular displacement of arrow 76 is a function of the relative viscosity of the mucus. In contrast to the operational characteristics of a concentric viscometer, the operational characteristics of the eccentric viscometer of the present invention are such that: (1) the mucus, which is displaced when outer bearing member 24 rotates, offers rotational resistance in addition to conventional shear due to the eccentrically disposed bearing surfaces; (2) the weight of outer bearing member 24 resists the torque; and (3) the dimensions of gap 54 varies during rotation.

One process of the present invention involves the use of sterile inner and outer bearing members 22, 24 as follows. First, inner bearing member 22 is assembled with chuck 34 by inserting extension 42 into opening 34. Next, chuck 34 is rotated until arrow 76 points to the zero marking on scale 78. Next, a sample 80 of cervical mucus is obtained by inserting a disposable probe 82 having an elastomeric scoop 84 at its extremity through the vaginal cavity into contact with the cervix in order to retain the sample of cervical mucus. Next, this cervical mucus is transferred to one of bearing surfaces 44, 52 and the inner and outer bearing members are assembled by fitting outer bearing member 24 onto inner bearing member 22, the arrangement being such that the cervical mucus is extruded between the bearing surfaces. Outer bearing member 24 is positioned so that arm 70 engages notch 72, the longitudinal axis of rod 56 being perpendicular with respect to the longitudinal axis of handle 64. Then, trigger 68 is pressed inwardly and release mechanism 68 is actuated to the unlocked position. During the time of ovulation, the mucus is watery and the rotational resistance is minimum. In consequence, when release mechanism 36 is actuated to the unlocked position, rod 56 rotates clockwise and arrow 76 remains stationary. At other times, the mucus is highly viscous and the rotational resistance is maximum. In consequence, when the release mechanism is in the unlocked position, rod 56 remains stationary and arrow 56 rotates clockwise. Finally, the position of arrow 76, a comparative indication of viscosity, denotes the presence or absence of ovulation. In ths process, the weight of outer bearing member 24 is 48 grams. The quantity of cervical mucus displaced as ring 58 travels in a 90° arcuate path is in the range of 3 to 5 mg, the mucus being positively displaced without homogenation of the mucus or the destruction of its viscoelastic properties during the measurement.

In an alternative process, oral mucus, i.e. saliva, is removed from the mouth by an eye dropper 86 having a tube 88 with a restricted end 90 and an elastomeric bulb 92. Here, saliva is applied to one of bearing surfaces 44, 52 simply by manually squeezing bulb 92 and extruding saliva through opening 90. This process otherwise is identical to that described above in connection with cervical mucus. In this process, the weight of outer bearing member 24 is 10 grams.

The embodiment of FIGS. 7 and 8 includes an elongated cylindrical probe 100, at the forward extremity of which is a cylindrical extension 102 of reduced diameter that is isolated from the remainder of the probe by a shoulder 104. The forward extremity of extension 102 is rounded as at 106. Associated with probe 100 is an annulus 108 having an inner bore 110 and forward and rearward flat parallel faces 112, 114. The outer bearing surface of extension 102 and the inner bearing surface of bore 110 snugly fit each other when ring 108 and probe 100 are assembled, a crescent shaped gap 115 being formed between the bearing surfaces. Extending from the periphery of ring 108 is a threaded shaft 116 having turned thereon an adjustable nut 118, the shaft and the nut serving as an adjustable torque weight. Probe 100 and ring 108 are composed of the same materials as are their counterparts in FIGS. 3 and 4. Also the dimensions and grit characteristics of extension bearing surface 102 and of bore bearing surface 110 are the same as are their counterparts in FIGS. 3 and 4.

In operation of the device of FIGS. 7 and 8, first probe 100 is inserted into the vaginal cavity so that extension 102 contacts the cervix, by which a quantity of cervical mucus is retained on the bearing surface of extension 102. Next probe 100 is withdrawn from the vaginal cavity and is assembled with ring 108 so that extension 102 is inserted into bore 110 and rearward movement of ring 108 is limited by shoulder 104. At this point cervical mucus is extruded between the bearing surfaces of bore 110 and extension 102. Then a user, while holding probe 100 horizontally in one hand, moves shaft 116 into horizontal orientation with the other hand. Finally when shaft 116 is released, eccentric rotation of ring 108 relative to probe 100 under the torque of weight 118 will or will not occur. Menstrual cycle phase thereby will be indicated in accordance with the present invention.

Since certain changes may be made in the present disclosure without departing from the scope of the present invention, it is intended that all matter described in the foregoing specification and depicted in the accompanying drawings be interpreted in an illustrative and not in a limiting sense.

What is claimed is:

1. A device for testing mucus from a boidly cavity, said device comprising an inner bearing element and an outer bearing element constrained for relative eccentric rotational motion with respect to each other, means for biasing said elements for said eccentric rotational motion, and means for indicating the occurrence of such motion, said inner bearing element and said outer bearing element having inner and outer, horizontally disposed, cylindrical bearing surfaces, said relative motion being a rotational movement about eccentric bearing surface axes that is related to both shear and displacement of said mucus.

2. The device of claim 1 wherein the difference between the diametral profiles of said bearing surfaces ranges from 0.01 to 10.0 mils, a crescent shaped gap formed between said bearing surfaces.

3. The device as claimed in claim 1 wherein each of said bearing surfaces has a surface finish ranging from 8 to 125 microinches in valley to peak height.

4. A device for testing mucus from a bodily cavity, said device comprising a support, inner bearing means and outer bearing means constrained for relative eccentric rotational motion with respect to each other on said support, means for releasably holding at least one of said inner bearing means and said outer bearing means against said motion, means for biasing said inner bearing means and said outer bearing means for said motion, and means for indicating the occurrence of such motion, said inner bearing means and said outer bearing means having inner and outer, substantially horizontally disposed, cylindrical bearing surfaces, said relative motion being a rotational movement about eccentric bearing surface axes that is related to both shear and displacement of said mucus, each of said bearing surfaces having a surface finish ranging from 8 to 125 microinches in valley to peak height.

5. The device of claim 4 wherein the difference between the diametral profiles of said bearing surfaces ranges from 0.01 to 10.0 mils, a gap formed between said bearing surfaces.

6. The device as claimed in claim 5 wherein said gap is crescent shaped.

7. The device of claim 4 wherein said inner bearing means is rotatably mounted to said base and said outer bearing means is rotatable eccentrically on said inner bearing means.

8. The device of claim 4 wherein aid inner bearing means and said outer bearing means are detachable from said support and from each other in one phase of operation and being attached to said support and to each other in another phase of operation.

9. The device of claim 4 wherein said means for indicating includes indicia on one of said bearing elements and indicia fixed in operation with respect to said support.

10. A process for testing mucus from a bodily cavity, said process comprising the steps of placing said mucus on one of an inner bearing element and an outer bearing element, constraining said inner bearing element and said outer bearing element for relative eccentric rotational motion with respect to each other, biasing said elements for said motion, and indicating the occurrence of such motion, said inner and outer substantially horizontally disposed, cylindrical bearing surfaces, said relative motion being a rotational movement about eccentric movement about eccentric bearing surface axes that is related to both shear and displacement of said mucus, each of said bearing surfaces having a surface finish ranging from 8 to 125 microinches in valley to peak height.

11. The process of claim 10 wherein the difference between the diametral profiles of said bearing surfaces ranges from 0.01 to 10.0 mils.

12. A device for testing mucus from a bodily cavity, said device comprising a support, inner bearing means and outer bearing means composed of glass, said inner bearing means and said outer bearing means constrained for relative eccentric rotational motion with respect to each other on said support, means for biasing said inner bearing means and said outer bearing means for said motion, means for releasably holding said inner bearing means and said outer bearing means against said motion, and means for indicating the occurrence of said motion, said inner bearing means and said outer bearing means having inner and outer cylindrical bearing surfaces, each of said bearing surfaces being substantially horizontal and having a surface finish ranging from 8 to 125 microinches in valley to peak height, said bearing surface disposed eccentrically relative to each other, said relative motion being a rotational movement about eccentric bearing surface axes that is related to both shear and displacement of said mucus, the difference between the diametral profiles of said bearing surfaces ranging from 0.01 to 10.0 mils, said means for indicating including indicia movable with at least on of said bearing elements and indicia fixed in operation with respect to said base.

13. The device of claim 12 wherein said support includes a grip and a chuck, said inner bearing member removable retained by said chuck.

14. The device of claim 12 wherein said support includes an elongated rod, said inner bearing member projecting from said rod and being substantially coaxial therewith, said rod providing a shoulder for limiting axial movement of said outer bearing member with respect thereto.

* * * * *